United States Patent
Brammer et al.

(10) Patent No.: US 9,539,566 B2
(45) Date of Patent: Jan. 10, 2017

(54) CATALYST PREPARATION PROCESS

(71) Applicant: Dow Technology Investments LLC, Midland, MI (US)

(72) Inventors: Michael A. Brammer, Lake Jackson, TX (US); Rick B. Watson, Missouri City, TX (US); Avery L. Watkins, Pearland, TX (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 14/423,455

(22) PCT Filed: Aug. 15, 2013

(86) PCT No.: PCT/US2013/055048
§ 371 (c)(1),
(2) Date: Feb. 24, 2015

(87) PCT Pub. No.: WO2014/035673
PCT Pub. Date: Mar. 6, 2014

(65) Prior Publication Data
US 2015/0209773 A1    Jul. 30, 2015

Related U.S. Application Data

(60) Provisional application No. 61/694,329, filed on Aug. 29, 2012.

(51) Int. Cl.
*B01J 31/18*   (2006.01)
*C07C 45/50*   (2006.01)
*C07C 45/00*   (2006.01)

(52) U.S. Cl.
CPC .............. *B01J 31/185* (2013.01); *C07C 45/00* (2013.01); *C07C 45/50* (2013.01); *B01J 2231/321* (2013.01); *B01J 2531/822* (2013.01)

(58) Field of Classification Search
CPC ................ B01J 31/185; B01J 2531/822; B01J 2231/321; C07C 45/00; C07C 45/50
USPC .................................... 556/13, 420; 568/420
See application file for complete search history.

(56) References Cited

U.S. PATENT DOCUMENTS

| | | |
|---|---|---|
| 3,415,906 A | 12/1968 | Shepard et al. |
| 3,527,809 A | 9/1970 | Pruett et al. |
| 4,148,830 A | 4/1979 | Pruett et al. |
| 4,247,486 A | 1/1981 | Brewester et al. |
| 4,329,507 A | 5/1982 | Takeda et al. |
| 4,518,809 A | 5/1985 | Forster et al. |
| 4,528,403 A | 7/1985 | Tano et al. |
| 4,567,302 A | 1/1986 | Sivaramakrishnan |
| 4,567,306 A | 1/1986 | Dennis et al. |
| 4,599,206 A | 7/1986 | Billig et al. |
| 4,668,651 A | 5/1987 | Billig et al. |
| 4,717,775 A | 1/1988 | Billig et al. |
| 4,748,261 A | 5/1988 | Billig et al. |
| 4,769,498 A | 9/1988 | Billig et al. |
| 4,774,361 A | 9/1988 | Maher et al. |
| 4,835,299 A | 5/1989 | Maher et al. |
| 4,885,401 A | 12/1989 | Billig et al. |
| 5,113,022 A | 5/1992 | Abatjoglou et al. |
| 5,179,055 A | 1/1993 | Wink et al. |
| 5,202,297 A | 4/1993 | Lorz et al. |
| 5,235,113 A | 8/1993 | Sato et al. |
| 5,254,741 A | 10/1993 | Lorz et al. |
| 5,264,616 A | 11/1993 | Roeper et al. |
| 5,277,532 A | 1/1994 | Pazzaglia |
| 5,288,918 A | 2/1994 | Maher et al. |
| 5,312,996 A | 5/1994 | Packett |
| 5,360,938 A | 11/1994 | Babin et al. |
| 5,364,950 A | 11/1994 | Babin et al. |
| 5,391,801 A | 2/1995 | Sato et al. |
| 5,491,266 A | 2/1996 | Babin et al. |
| 5,527,950 A | 6/1996 | Hansen et al. |
| 5,684,167 A | 11/1997 | Omatsu et al. |
| 5,741,945 A | 4/1998 | Bryant et al. |
| 5,929,289 A | 7/1999 | Abatjoglou et al. |
| 6,153,800 A | 11/2000 | Gelling et al. |
| 7,262,330 B2 | 8/2007 | Ueda et al. |
| 7,495,134 B2 | 2/2009 | Hess et al. |
| 7,745,666 B2 | 6/2010 | Sugioka et al. |
| 7,863,487 B2 | 1/2011 | Eisenschmid et al. |
| 7,943,801 B2 | 5/2011 | Choi et al. |
| 2003/0171623 A1 | 9/2003 | Puckette et al. |
| 2010/0069680 A1 | 3/2010 | Eisenschmid et al. |
| 2012/0259142 A1 | 10/2012 | Eisenschmid et al. |

OTHER PUBLICATIONS

Guo, et al., "Hydroformylation of 1-hexene with Pt(P(m-C6H4SO3Na)3)2Cl2 and its tin chloride analogue on a controlled-pore glass", Journal of Molecular Catalysis, 1991, 70, p. 363-368.
Toth, et al., "Immobilization of HRh(CO)(P(m-C6H4SO3Na)3)3 on an Anion Exchange Resin for the Hydroformylation of Higher Olefins", Catalysis Letters, 1991, 8, p. 209-214.
Guo, et al., "Bis[tris(m-(sodium sulfonato)phenyl)phosphine] hexacarbonyl dicobalt, Co2(CO)6(P(m-C6H4SO3Na)3) 2, in a supported aqueous phase for the hydroformylation of 1-hexene", Journal of Organometallic Chemistry, 1991, 403, p. 221-227.
Arhancet, et al., "Hydroformylation by supported aqueous-phase catalysis: a new class of heterogeneous catalysist", Letters to Nature, Jun. 8 1989, 339, p. 454-455.
Rode, et al., "Propylene Hydroformylation on Rhodium Zeoltes X and Y", Journal of Catalysis, 1985, 96, p. 563-573.
Davis, et al., "Hydroformylation of 1-Hexene by Soluble and Zeolite-Supported Rhodium Species Part II", Journal of Molecular Catalysis, 1987, 39, p. 243-259.

(Continued)

*Primary Examiner* — Porfirio Nazario Gonzalez

(57) ABSTRACT

A process for forming a catalyst from a catalytic metal precursor, a chelating bisphosphite and a bulky monophosphite, with a slightly greater than stoichiometric amount of chelating bisphosphite relative to catalytic metal under a CO partial pressure at least 25 psig.

14 Claims, 1 Drawing Sheet

(56) References Cited

OTHER PUBLICATIONS

Feldman, et al., "Membrane-supported rhodium hydroformylation catalysts", Journal of Molecular Catalysis, 1990, 63, p. 213-221.
Jongsma, et al., "Fine tuning of bulky-phosphite modified rhodium catalysts by binding them to copolymers", Journal of Molecular Catalysis, 1993, 83, p. 17-35.
Milstein, et al., "Polymeric supports for catalysts", Chemtech, 13, No. 1, Jan. 1983, p. 46-53.
Parrinello, et al., "Asymmetric Hydroformylation Catalyzed by Homogeneous and Polymer-Supported Platinum Complexes Containing Chiral Phosphine Ligands", Journal American Chemical Society, 1987, 109, p. 7122-7127.
Jongsma, et al., "A new type of highly active polymer-bound rhodium hydroformylation catalyst", Polymer, 1992, 33, p. 161-165.
Bergbreiter, et al., "Polyethylene-Bound Soluble Recoverable Palladium (0) Catalysts", Journal of Organic Chemistry, 1989, 54, p. 2726-2730.
Lide, CRC Handbook of Chemistry and Physics, 1991-1992, 72nd Ed., CRC press, p. 1-10.
PCT/US2013/055048, 20131128, International Search Report and Written Opinion.
PCT/US2013/055048, 20150312, International Preliminary Report on Patentability.

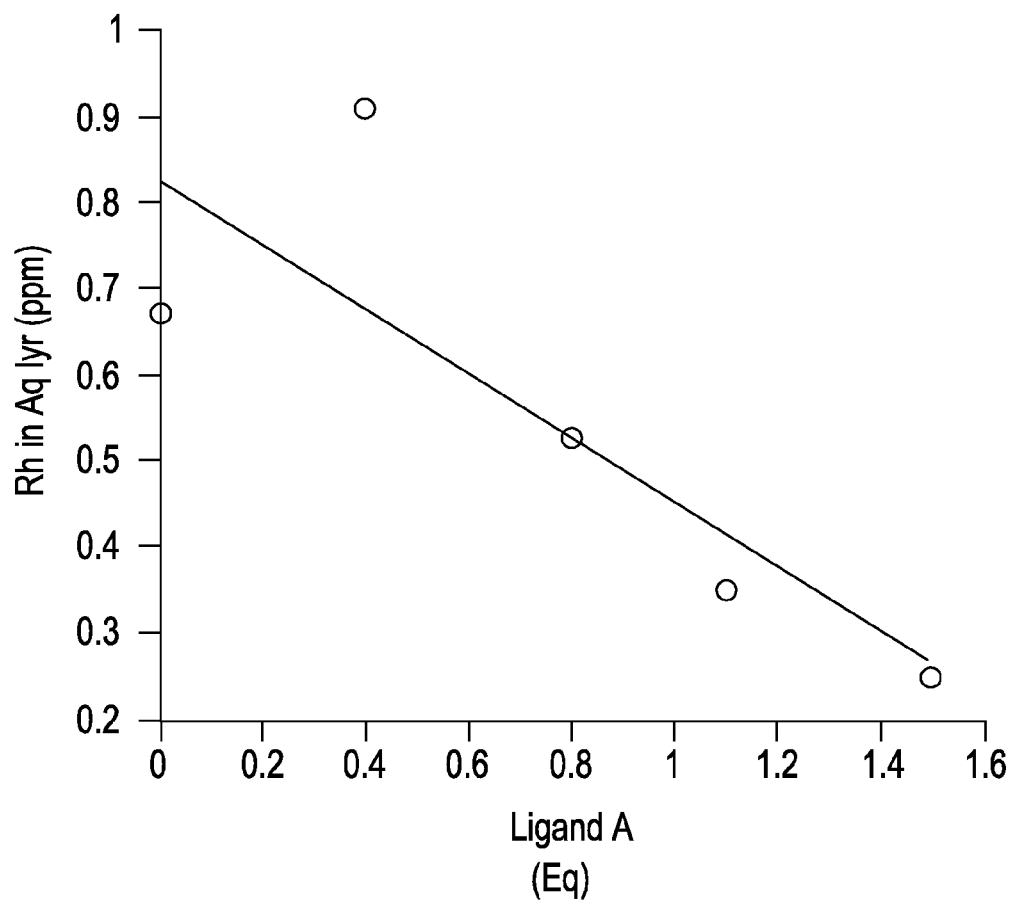

CATALYST PREPARATION PROCESS

CROSS-REFERENCE TO RELATED APPLICATIONS

This application claims priority from provisional application Ser. No. 61/694,329, filed Aug. 29, 2012, which is incorporated herein by reference in its entirety.

BACKGROUND OF THE INVENTION

The invention relates to a hydroformylation process that employs a organopolyphosphite ligand and an organomonophosphite ligand.

US 2010/0069680 teaches that hydroformylation reactions featuring a mixture of a chelating bisphosphite and a bulky monophosphite ligand, where the bisphosphite is employed at a less than stoichiometric amount relative to rhodium and the process is operated in the negative order region of the carbon monoxide partial pressure curve, can provide improved control of the product isomer ratio. This technology can allow practitioners to tailor their processes to meet shifting market and customer demands. However, when the components of such a mixed ligand system are initially charged to a reactor, the bisphosphite ligand rapidly coordinates to a portion of the rhodium, resulting in a stable rhodium-bisphosphite complex. In principal, the remaining rhodium is ligated by the bulky monophosphite; however, rhodium-bulky monophosphite complexes form at a relatively slow rate under hydroformylation conditions. Thus, in a reactor charged with rhodium and a bulky monophosphite alone or with a bulky monophosphite and a substoichiometric amount of bisphosphite, some portion of the rhodium may not initially be ligated. This results in a situation where valuable rhodium may be deposited or lost in parts of the process.

Increasing the concentration of the bulky monophosphite might appear to be a solution to this problem. However, many preferred bulky monophosphites are only modestly soluble in the reaction matrix, which limits their final concentration. Additionally phosphite ligand degradation reactions are typically positive order (i.e., the more ligand present, the faster it decomposes), which creates operational issues and increases cost when using a large excess of ligand. Thus, there exists a need for an improved process for forming a hydroformylation catalyst, which process would reduce the risk of losing valuable rhodium and reduce the risk of accelerated ligand degradation.

SUMMARY OF THE INVENTION

The invention is such a process comprising (A) forming a hydroformylation catalyst by contacting under reaction conditions, in the presence of a solvent, a catalytic metal precursor, at least one organopolyphosphite ligand, CO, hydrogen, a bulky organomonophosphite ligand and, optionally, an olefin, wherein: the molar organopolyphosphite-to-catalytic metal ratio is at least 1 but less than 2; the partial pressure of carbon monoxide is at least 25 psig (172 kPa); and the molar ratio of bulky organomonophosphite-to-catalytic metal is from 5:1 to 50:1; and then (B) allowing the organopolyphosphite ligand concentration to diminish such that the ratio of organopolyphosphite ligand-to-catalytic metal falls to less than 1.

Losses of valuable catalytic metal surprisingly are substantially reduced if the hydroformylation reaction is initiated with at least a stoichiometric amount of the chelating bisphosphite ligand relative to catalytic metal. The presence of an excess of the bulky monophosphite then allows a stable catalytic metal-bulky monophosphite complex to form as the chelating bisphosphite concentration slowly and naturally declines to the desired substoichiometric levels.

Surprisingly, the monophosphite ligand is more stable at high carbon monoxide partial pressures.

BRIEF DESCRIPTION OF THE DRAWINGS

FIG. 1 is graph of data from Example 7 showing the relationship of Ligand A concentration and rhodium loss.

DETAILED DESCRIPTION OF THE INVENTION

The invention involves forming a catalyst from a catalytic metal precursor, a chelating bisphosphite and a bulky monophosphite, with a slightly greater than stoichiometric amount of chelating bisphosphite relative to catalytic metal under a CO partial pressure at least 25 psig (172 kPa). The catalyst can be used in hydroformylation reactions, e.g., to prepare aldehydes from olefins.

All references to the Periodic Table of the Elements and the various groups therein are to the version published in the CRC Handbook of Chemistry and Physics, 72nd Ed. (1991-1992) CRC Press, at page I-10.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means part per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to 20 or more, preferably from 1 to 12. The permissible substituents can be one or more and the same or different for appropriate organic compounds. This invention is not intended to be limited in any manner by the permissible substituents of organic compounds.

As used herein, the term "hydroformylation" is contemplated to include, but not limited to, all permissible asymmetric and non-asymmetric hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes.

The terms "reaction fluid," "reaction medium" and "catalyst solution" are used interchangeably herein, and include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds formed in the reaction (which may be homogeneous or heterogeneous, and these compounds include those adhered to process equipment surfaces). The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an aqueous buffer solution, (g) a treated fluid returned to a reaction zone or separation zone, (h) a fluid in an external cooler, and (i) ligand decomposition products and their salts.

The catalytic metal precursor can be any source of catalytic metal suitable for the catalyst formation reaction. The metals can include Group 8, 9 and 10 metals selected from rhodium (Rh), cobalt (Co), iridium (Ir), ruthenium (Ru), iron (Fe), nickel (Ni), palladium (Pd), platinum (Pt), and osmium (Os), with the preferred metals being rhodium, cobalt, iridium and ruthenium, more preferably rhodium, cobalt and ruthenium, most preferably rhodium. Mixtures of these metals may be used. Examples of the catalytic metal precursor include rhodium source materials such as rhodium acetylacetonate, rhodium dicarbonyl acetylacetonate, $Rh_2O_3$, $Rh_4(CO)_{12}$, $[RhCl(CO)_2]_2$, $Rh_6(CO)_{16}$, and $Rh(NO_3)_3$.

The permissible organophosphorous ligands that make up the metal-organophosphorous ligand complexes and free organophosphorous ligand include mono-, di-, tri- and higher polyorganophosphorus ligands. Mixtures of ligands may be employed in the metal-organophosphorous ligand complex catalyst and/or free ligand, and such mixtures may be the same or different.

Hydrogen and carbon monoxide may be obtained from any suitable source, including petroleum cracking and refinery operations. Syngas mixtures are a preferred source of hydrogen and CO. Syngas (from synthesis gas) is the name given to a gas mixture that contains varying amounts of CO and $H_2$. Production methods are well known. Hydrogen and CO typically are the main components of syngas, but syngas may contain $CO_2$ and inert gases such as $N_2$ and Ar. The ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO ratio for chemical production is between 3:1 and 1:3 and usually is targeted to be between about 1:2 and 2:1 for most hydroformylation applications.

The catalyst formation process optionally employs an olefin. Advantageously, the olefin is an olefin that is intended to be used in the hydroformylation reaction catalyzed by the formed catalyst.

The substituted or unsubstituted olefinic unsaturated reactants that may be employed in the hydroformylation process include both optically active (prochiral and chiral) and non-optically active (achiral) olefinic unsaturated compounds containing from 2 to 40, preferably 3 to 20, carbon atoms. These compounds are described in detail in US 2010/006980. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403).

Prochiral and chiral olefins useful in the asymmetric hydroformylation that can be employed to produce enantiomeric aldehyde mixtures include those represented by the formula:

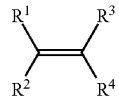

wherein $R^1$, $R^2$, $R^3$ and $R^4$ are the same or different (provided that $R^1$ is different from $R^2$ or $R^3$ is different from $R^4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, and carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene, and the like.

Illustrative optically active or prochiral olefinic compounds useful in asymmetric hydroformylation are described, for example, in U.S. Pat. Nos. 4,329,507, 5,360,938 and 5,491,266.

The organophosphorous compounds that may serve as the ligand of the metal-organophosphorous ligand complex catalyst and/or free ligand may be of the achiral (optically inactive) or chiral (optically active) type and are well known in the art. Achiral organophosphorous ligands are preferred.

Among the organophosphorous ligands that may serve as the ligand of the metal-organophosphorous ligand complex catalyst are monoorganophosphite, diorganophosphite, triorganophosphite and organopolyphosphite compounds. Such organophosphorous ligands and methods for their preparation are well known in the art.

The bulky organomonophosphorus ligands useful in this invention: (i) have a coordination strength with respect to the metal of said metal-organopolyphosphite ligand complex catalyst less than the organopolyphosphite ligand of said metal-organopolyphosphite ligand complex catalyst, (ii) do not inhibit the organopolyphosphite ligand complex catalyst by more than 25% as measured by comparing reaction rates with and without the bulky organomonophosphorus ligands in the reaction of interest, (iii) have a coordination strength with respect to the metal of said metal-organopolyphosphite ligand complex catalyst greater than CO, and (iv) are sterically hindered. For the purposes of the invention, a "sterically hindered" ligand is a ligand with a Tolman steric parameter of 135 to 190° as described in U.S. Pat. No. 5,684,167.

In one embodiment of the invention, when complexed with the metal to form a metal-bulky organophosphorus ligand complex catalyst, the bulky organomonophosphorus ligand enables a normal:branched product isomer (N:I) ratio different from the N:I ratio provided by a metal-sterically hindered organophosphorus ligand complex catalyst formed from the organopolyphosphite ligand.

In a preferred embodiment, the bulky organomonophosphorus ligand can be any of the ligands, e.g., organomonophosphite ligands, represented by formulas (I) through (IV) below, provided that such bulky organomonophosphorus ligand meets the criteria set forth herein. Preferred bulky organomonophosphorus phosphite ligands include diorganophosphites and oxides, e.g., monoxides, of organobisphosphites.

Representative monoorganophosphites may include those having the formula:

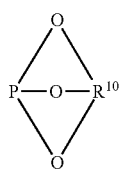

<<I>> wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, for example, in U.S. Pat. No. 4,567,306.

Representative diorganophosphites may include those having the formula:

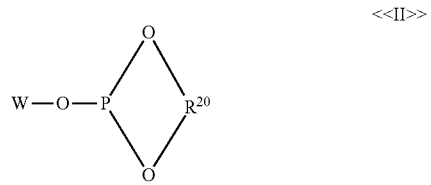

<<II>> wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, cycloalkylene radicals, and, alkylene-$NR^{24}$-alkylene wherein $R^{24}$ is hydrogen or a substituted or unsubstituted monovalent hydrocarbon radical, e.g., an alkyl radical having 1 to 4 carbon atoms. The more preferred divalent acyclic radicals are the divalent alkylene radicals such as disclosed more fully, for example, in U.S. Pat. Nos. 3,415,906 and 4,567,302. Illustrative divalent aromatic radicals include, for example, arylene, bisarylene, arylene-alkylene, arylene-alkylene-arylene, arylene-oxy-arylene, arylene-$NR^{24}$-arylene wherein $R^{24}$ is as defined above, arylene-S-arylene, and arylene-S-alkylene, and the like. More preferably $R^{20}$ is a divalent aromatic radical such as disclosed more fully, for example, in U.S. Pat. Nos. 4,599,206, 4,717,775, 4,835,299, and the like.

Representative of a more preferred class of diorganophosphites are those of the formula:

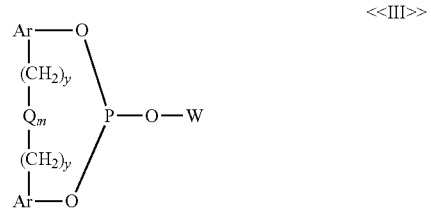

<<III>> wherein W is as defined above, each Ar is the same or different and represents a substituted or unsubstituted aryl radical, each y is the same or different and is a value of 0 or 1, Q represents a divalent bridging group selected from —$C(R^{33})_2$—, —O—, —S—, —$NR^{24}$—, $Si(R^{35})_2$ and —CO—, wherein each $R^{33}$ is the same or different and represents hydrogen, an alkyl radical having from 1 to 12 carbon atoms, phenyl, tolyl, and anisyl, $R^{24}$ is as defined above, each $R^{35}$ is the same or different and represents hydrogen or a methyl radical, and m has a value of 0 or 1. Such diorganophosphites are described in greater detail, for example, in U.S. Pat. Nos. 4,599,206, 4,717,775, and 4,835,299.

Representative triorganophosphites may include those having the formula:

(IV)

wherein each $R^{46}$ is the same or different and is a substituted or unsubstituted monovalent hydrocarbon radical e.g., a cycloalkyl, aryl, or aralkyl radicals that may contain from 1 to 24 carbon atoms. Illustrative triorganophosphites include aryl phosphites such as, for example, trinaphthyl phosphite, bis(3,6,8-tri-t-butyl-2-naphthyl)methylphosphite, bis(3,6,8-tri-t-butyl-2-naphthyl)cyclohexylphosphite, tris(3,6-di-t-butyl-2-naphthyl)phosphite, bis(3,6,8-tri-t-butyl-2-naphthyl)phenylphosphite, and bis(3,6,8-tri-t-butyl-2-naphthyl)(4-sulfonylphenyl)phosphite. The most preferred triorganophosphite is tris(2,4-di-t-butylphenyl)phosphite. Such triorganophosphites are described in greater detail, for example, in U.S. Pat. Nos. 3,527,809, 5,277,532 and 5,684,167.

Representative organopolyphosphites contain two or more tertiary (trivalent) phosphorus atoms and may include those having the formula:

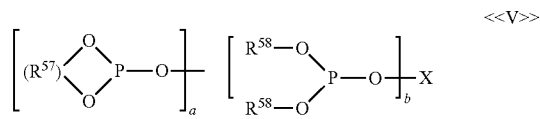

(V)

wherein X represents a substituted or unsubstituted n-valent organic bridging radical containing from 2 to 40 carbon atoms, each $R^{57}$ is the same or different and represents a divalent organic radical containing from 4 to 40 carbon atoms, each $R^{58}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^{57}$ radical may be the same or different. Each $R^{58}$ radical may also be the same or different in any given compound.

Representative n-valent (preferably divalent) organic bridging radicals represented by X and representative divalent organic radicals represented by $R^{57}$ above, include both acyclic radicals and aromatic radicals, such as alkylene, alkylene-$Q_m$-alkylene, cycloalkylene, arylene, bisarylene, arylene-alkylene, and arylene-$(CH_2)_y$-$Q_m$-$(CH_2)_y$-arylene radicals, and the like, wherein each Q, y and m are as defined above in Formula (III). The more preferred acyclic radicals represented by X and $R^{57}$ above are divalent alkylene radicals, while the more preferred aromatic radicals represented by X and $R^{57}$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616 and 5,364,950, and 5,527,950. Representative preferred monovalent hydrocarbon radicals represented by each $R^{58}$ radical above include alkyl and aromatic radicals.

Illustrative preferred organopolyphosphites may include bisphosphites such as those of Formulas (VI) to (VIII) below:

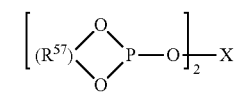

(VI)

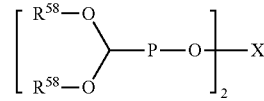

(VII)

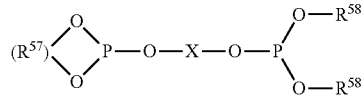

(VIII)

wherein each $R^{57}$, $R^{58}$ and X of Formulas (VI) to (VIII) are the same as defined above for Formula (V). Preferably each $R^{57}$ and X represents a divalent hydrocarbon radical selected from alkylene, arylene, arylene-alkylene-arylene, and bisarylene, while each $R^{58}$ radical represents a monovalent hydrocarbon radical selected from alkyl and aryl radicals. Organophosphite ligands of such Formulas (V) to (VIII) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801.

$R^{10}$, $R^{20}$, $R^{46}$, $R^{57}$, $R^{58}$, Ar, Q, X, m, and y in Formulas (VI) to (VIII) are as defined above. Most preferably X represents a divalent aryl-$(CH_2)_y$-$(Q)_m$-$(CH_2)_y$-aryl radical wherein each y individually has a value of 0 or 1; m has a value of 0 or 1 and Q is —O—, —S— or —C$(R^{35})_2$— where each $R^{35}$ is the same or different and represents hydrogen or a methyl radical. More preferably each alkyl radical of the above defined $R^8$ groups may contain from 1 to 24 carbon atoms and each aryl radical of the above-defined Ar, X, $R^{57}$ and $R^{58}$ groups of the above Formulas (VI) to (VII) may contain from 6 to 18 carbon atoms and said radicals may be the same or different, while the preferred alkylene radicals of X may contain from 2 to 18 carbon atoms and the preferred alkylene radicals of $R^{57}$ may contain from 5 to 18 carbon atoms. In addition, preferably the divalent Ar radicals and divalent aryl radicals of X of the above formulas are phenylene radicals in which the bridging group represented by —$(CH_2)_y$-$(Q)_m$-$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Of course any of the $R^{10}$, $R^{20}$, $R^{57}$, $R^{58}$, W, X, Q and Ar radicals of such organophosphites of Formulas (I) to (VIII) above may be substituted if desired, with any suitable substituent containing from 1 to 30 carbon atoms that does not unduly adversely affect the desired result of the process of this invention. Substituents that may be on said radicals in addition of course to corresponding hydrocarbon radicals such as alkyl, aryl, aralkyl, alkaryl and cyclohexyl substituents, may include for example silyl radicals such as —Si$(R^{35})_3$; amino radicals such as —N$(R^{15})_2$; phosphine radicals such as -aryl-P$(R^{15})_2$; acyl radicals such as —C(O)$R^{15}$ acyloxy radicals such as —OC(O)$R^{15}$; amido radicals such as —CON$(R^{15})_2$ and —N$(R^{15})$COR$^{15}$; sulfonyl radicals such as —SO$_2$R$^{15}$, alkoxy radicals such as —OR$^{15}$; sulfinyl radicals such as —SOR$^{15}$, sulfonyl radicals such as —SR$^{15}$, phosphonyl radicals such as —P(O)(R$^{15}$)$_2$, as well as halo, nitro, cyano, trifluoromethyl, hydroxy radicals, and the like, wherein each R$^{15}$ radical individually represents the same or different monovalent hydrocarbon radical having from 1 to 18 carbon atoms (e.g., alkyl, aryl, aralkyl, alkaryl and cyclohexyl radicals), with the proviso that in amino substituents such as —N(R$^{15}$)$_2$ each R$^{15}$ taken together can also represent a divalent bridging group that forms a heterocyclic radical with the nitrogen atom, and in amido substituents such as —C(O)N(R$^{15}$)$_2$ and —N(R$^{15}$)COR$^{15}$ each R$^{15}$ bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neopentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —OCH$_2$CH$_2$OCH$_3$, —O(CH$_2$CH$_2$)$_2$OCH$_3$, —O(CH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$), and the like; arylphosphine radicals such as —P(C$_6$H$_5$)$_2$, and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like; amido radicals such as —CONH$_2$, —CON(CH$_3$)$_2$, —NHC(O)CH$_3$, and the like; sulfonyl radicals such as —S(O)$_2$C$_2$H$_5$ and the like; sulfinyl radicals such as —S(O)CH$_3$ and the like; sulfonyl radicals such as —SCH$_3$, —C$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), —P(O)(H)(C$_6$H$_5$), and the like.

Specific illustrative examples of such organophosphite ligands include the following: 2-t-butyl-4-methoxyphenyl(3,3'-di-t-butyl-5,5'-dimethoxy-1,1'-biphenyl-2,2'-diyl)phosphite, methyl(3,3'-di-t-butyl-5,5'-dimethoxy-1,1'-biphenyl-2,2'-diyl)phosphite, 6,6'-[[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin, 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin, (2R,4R)-di[2,2'-(3,3',5,5'-tetrakis-tert-butyl-1,1-biphenyl)]-2,4-pentyldiphosphite, (2R,4R)di[2,2'-(3,3'-di-tert-butyl-5,5'-dimethoxy-1,1'-biphenyl)]-2,4-pentyldi phosphite, 2-[[2-[[4,8,-bis(1,1-dimethylethyl), 2,10-dimethoxydibenzo-[d,f][1,3,2]dioxaphosphepin-6-yl]oxy]-3-(1,1-dimethylethyl)-5-methoxyphenyl]methyl]-4-methoxy, methylenedi-2,1-phenylene tetrakis[2,4-bis(1,1-dimethylethyl)phenyl]ester of phosphorous acid, and [1,1'-biphenyl]-2,2'-diyl tetrakis[2-(1,1-dimethylethyl)-4-methoxyphenyl]ester of phosphorous acid.

The organopolyphosphite ligands have a coordination strength, relative to the catalytic metal, that is greater than that of the bulky organophosphorus ligand.

The active catalyst can be derived from the catalytic metal precursor that may be introduced into the reaction medium for in situ formation of the active catalyst. For example, a rhodium catalyst precursor may be introduced into the reaction mixture along with the organophosphorous ligands for the in situ formation of the active catalyst. In a preferred embodiment, rhodium dicarbonyl acetylacetonate is employed as a rhodium precursor and reacted in the presence of a solvent, initially with the organopolyphosphite ligand to form a rhodium-organopolyphosphite ligand complex in the presence of excess (free) bulky organomonophosphite ligand under syngas pressure for the in situ formation of the active catalyst.

In addition to the active catalyst, free bulky organomonophosphorous ligand (i.e., ligand that is not complexed with the metal) is also present in the reaction medium Said amounts of bulky organomonophosphorous ligand are the sum of both the amount of bulky organomonophosphorous ligand that is bound (complexed) to the metal present and the amount of free bulky organomonophosphorous ligand present. As desired, additional bulky organomonophosphorous ligand can be supplied to the reaction medium of the hydroformylation process at any time and in any suitable manner, e.g., to maintain a predetermined level of free ligand in the reaction medium.

In one embodiment, the rhodium catalyst may be impregnated onto any solid support, such as inorganic oxides, (i.e., alumina, silica, titania, or zirconia) carbon, or ion exchange resins, supported on, or intercalated inside the pores of, a zeolite, glass or clay, or may also be dissolved in a liquid film coating the pores of said zeolite or glass. Such zeolite-supported catalysts are particularly advantageous for producing one or more regioisomeric aldehydes in high selectivity, as determined by the pore size of the zeolite. The solid catalyst thus formed may still be complexed with one or more of the ligands defined above. Descriptions of such solid catalysts may be found in for example: *J. Mol. Cat.* 1991, 70, 363-368; *Catal. Lett.* 1991, 8, 209-214; *J. Organomet. Chem,* 1991, 403, 221-227; *Nature,* 1989, 339, 454-455; *J. Catal.* 1985, 96, 563-573; *J. Mol. Cat.* 1987, 39, 243-259. The catalyst may be attached to a thin film or membrane support, such as cellulose acetate or polyphenylenesulfone, as described in, for example, *J. Mol. Cat.,* 1990, 63, 213-221. The catalyst may be attached to an insoluble polymeric support through an organophosphorus-containing ligand, such as a phosphite, incorporated into the polymer. Descriptions of polymer-supported catalysts may be found in for example: *J. Mol. Cat.,* 1993, 83, 17-35; *Chemtech* 1983, 46; *J. Am. Chem. Soc.,* 1987, 109, 7122-7127. In another embodiment, the catalyst may be supported on a polymer that, by the nature of its molecular weight, is soluble in the reaction medium at elevated temperatures, but precipitates upon cooling, thus facilitating catalyst separation from the reaction mixture. Such "soluble" polymer-supported catalysts are described in for example: *Polymer,* 1992, 33, 161; *J. Org. Chem.* 1989, 54, 2726-2730.

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit Illustrative preferred solvents include ketones (e.g., acetone and methylethyl ketone), esters (e.g., ethyl acetate, di-2-ethylhexyl phthalate, 2,2,4-trimethyl-1,3-pentanediol monoisobutyrate), hydrocarbons (e.g., toluene), nitrohydrocarbons (e.g., nitrobenzene), ethers (e.g., tetrahydrofuran (THF)) and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. No. 4,148,380 and U.S. Pat. No. 4,247,486. The primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of solvents may be employed.

The active catalyst is prepared in situ by combining the catalytic metal precursor with the organopolyphosphite ligand and the bulky organomonophosphite ligand in a suitable solvent under syngas pressure. In one embodiment of the invention, the organopolyphosphite and the catalytic metal precursor advantageously are charged to the reactor prior to the addition of the bulky organomonophosphite. In a preferred embodiment the organopolyphosphite ligand is first added to the solvent, followed by the catalytic metal precursor, and finally the bulky organomonophosphite.

Without being bound by any theory, it is believed that, because the metal-organopolyphosphite complex forms very quickly, the time that elapses prior to the bulky organomonophosphite being added is not critical; indeed the bulky organomonophosphite may optionally be added along with the organopolyphosphite.

In another embodiment, when the catalytic metal becomes depleted or deactivated during normal use and it is necessary to add more to an existing catalyst solution, the catalyst make-up charge should be performed as described herein as if it was the initial catalyst charge. In other words, the catalyst makeup charge is generated by adding the organopolyphosphite and the catalytic metal precursor to the bulky organomonophosphite (optionally in a separate catalyst mixing tank prior to being introduced to the hydroformylation reaction system).

Advantageously, the amount of catalytic metal precursor ranges from 10 ppmw to 1000 ppmw, calculated as free metal in the reaction medium, while it is generally preferred to employ from 25 to 500 ppmw of metal, and more preferably from 50 to 350 ppmw of catalytic metal.

The amount of organopolyphosphite employed should be at least 1 but less than 2 moles per mole of catalytic metal. In one embodiment of the invention, the molar organopolyphosphite-to-catalytic metal ratio is from 1.05 to 1.8, and in another embodiment is from 1.08 to 1.2.

The concentration of the bulky organomonophosphite may vary, but advantageously ranges from about 5 to 50 moles per mole of catalytic metal. In a preferred embodiment, the concentration of bulky organomonophosphite is about 20 to 30 moles per mole of catalytic metal.

Once the organopolyphosphite, catalytic metal and bulky organomonophosphite have been combined in the proper proportions, syngas is introduced. The partial pressure of carbon monoxide advantageously is at least 25 psig (172 kPa). In one embodiment of the invention, the partial pressure of CO is at least 30 psig (207 kPa), In one embodiment of the invention, the partial pressure of CO is no more than 250 psig (1724 kPa). The pressure of syngas employed may vary so long as the partial pressure of CO is within the range described above. In a preferred embodiment the syngas partial pressure is from 50 psig 345 lPa) to 500 psig (3450 kPa).

An olefin can optionally be employed in the process of the invention.

The catalyst formed by the process of the invention is useful in hydroformylation reactions involving CO, $H_2$, and an olefin. The hydroformylation process, and conditions for its operation, are well known.

In general, the hydroformylation process may be conducted at any operable reaction temperature. Advantageously, the hydroformylation process is conducted at a reaction temperature from $-25°$ C. to $200°$ C., preferably from $50°$ C. to $120°$ C.

Metal-organophosphorous ligand complex catalysts are well known in the art and include those disclosed in the patents mentioned herein. However, the exact structure of the catalyst is not known. The metal-organophosphorous ligand complex catalyst can be optically active or non-optically active.

SPECIFIC EMBODIMENTS OF THE INVENTION

The following examples are given to illustrate the invention and should not be construed as limiting its scope.

General Procedure

A liquid recycle reactor system is employed that consists of three 1 liter stainless steel stirred tank reactors connected in series. Each reactor is equipped with a vertically mounted agitator and a circular tubular sparger located near the bottom of the reactor. Each sparger contains a plurality of holes of sufficient size to provide the desired gas flow into the liquid body in the reactor. The spargers are used for feeding the olefin and/or syngas to the reactor, and can also be used to introduce unreacted gases to each reactor. Each reactor has a silicone oil shell as a means of controlling reactor temperature. Reactors 1 to 2 and reactors 2 to 3 are further connected via lines to transfer any unreacted gases and lines to allow a portion of the liquid solution containing aldehyde product and catalyst to be pumped from reactor 1 to reactor 2 and from reactor 2 to reactor 3. Hence, the unreacted olefin of reactor 1 is further hydroformylated in reactor 2 and subsequently reactor 3. Each reactor also contains a pneumatic liquid level controller for maintaining the desired liquid level. Reactor 3 has a blow-off vent for removal of unreacted gases.

A portion of the liquid reaction solution is continuously pumped from Reactor 3 to a vaporizer, which consists of a heated vessel at reduced pressure. The effluent stream from the vaporizer is sent to a separator gas-liquid separator located at the bottom of the vaporizer, where vaporized aldehyde is separated from the non-volatile components of the liquid reaction solution. The vaporized aldehyde product is condensed and collected in a product receiver. A pneumatic liquid level controller controls the desired non-volatile component level, including catalyst to be recycled, at the bottom of the separator. The separator is connected to the buffer treatment vessel by a recycle line.

The non-volatile components, including catalyst to be recycled, from the separator are passed into the bottom of an aqueous buffer treatment packed column, which consists of a contacting region and a phase separation zone. Following the buffer treatment, the organic non-volatile layer, which contains catalyst to be recycled, is pumped from the phase separation zone through a recycle line into Reactor 1.

Comparative Experiment 1

LIGAND B Usage as a Function of Carbon Monoxide Partial Pressure. (Not an Embodiment of the Invention)

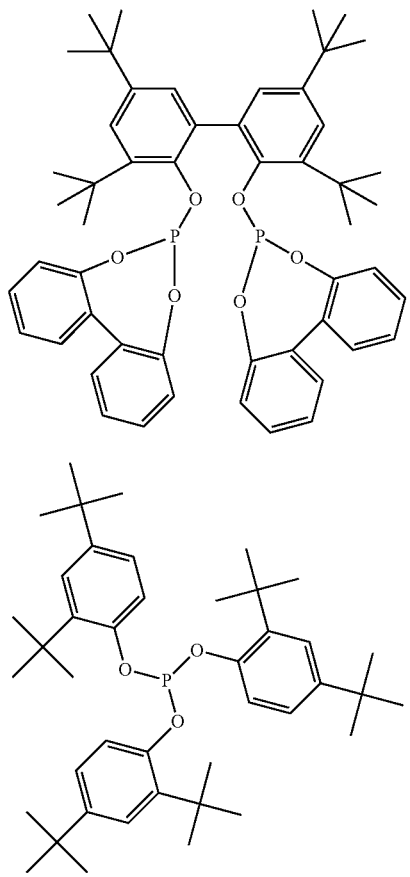

Ligand A

Ligand B

The hydroformylation reaction is conducted by charging to the reactor system 3 liters of catalyst solution comprising rhodium dicarbonyl acetylacetonate (55 ppm rhodium), LIGAND A (0.0149 wt %; 0.33 mole equivalents per mole rhodium) LIGAND B (0.70 wt %; 20 mole equivalents per rhodium), tetraethylene glycol dimethyl ether (about 15% by weight) and mixed $C_4$ aldehyde (about 85% by weight: n-butyraldehyde to iso-butyraldehyde ratio of about 30:1). The reactors are then heated to 70° C. under flowing carbon monoxide and hydrogen; the partial pressures of hydrogen and carbon monoxide are maintained at a 1:1 ratio over a range of 120 to 160 psig (827 to 1103 kPa). Reactor 1, 2 and 3 total pressures are maintained at 200, 180, and 160 psig (1379, 1241, and 1103 kPa) respectively. Propylene is fed to Reactor 1 at a rate of 1.8 gram moles per liter of total reactor volume per hour. The vaporizer system is operated at 6 to 8 psig (41 to 55 kPa) and 96 to 100° C. The above mentioned reaction conditions are maintained throughout unless otherwise indicated. The normal to iso-butyraldehyde ratio (N:I) is controlled at ~2 by maintaining a constant concentration of LIGAND A and LIGAND B The partial pressure of carbon monoxide is varied during the hydroformylation and the concentrations of LIGAND A and LIGAND B are measured by high pressure liquid chromatography (HPLC). LIGAND-B usage rates (i.e., the amount of LIGAND B that must be added each day to maintain a constant concentration) is calculated from the HPLC data and is presented in Table 1.

TABLE 1

LIGAND B Usage Rates as a Function of CO Partial Pressure.

| Days on-line | Average CO Partial Pressure (psig) [kPa] | Daily usage of LIGAND B (g/L/day) |
|---|---|---|
| 5 | 72.4 [499] | 0.011 |
| 7 | 67.7 [467] | 0.056 |
| 10 | 65.5 [452] | 0.048 |
| 19 | 59.6 [411] | 0.036 |
| 21 | 59.2 [408] | 0.032 |
| 24 | 55.9 [385] | 0.075 |
| 26 | 51.6 [356] | 0.078 |
| 28 | 52.2 [360] | 0.059 |
| 31 | 54.0 [372] | 0.052 |
| 34 | 38.0 [262] | 0.451 |
| 35 | 38.0 [262] | 0.259 |
| 38 | 37.5 [259] | 0.241 |
| 40 | 38.6 [266] | 0.170 |
| 42 | 67.3 [464] | 0.059 |
| 45 | 66.1 [456] | 0.040 |
| 49 | 64.4 [458] | 0.034 |
| 59 | 63.2 [436] | 0.039 |
| 61 | 63.2 [436] | 0.024 |
| 63 | 62.8 [433] | 0.016 |
| 67 | 58.9 [406] | 0.013 |
| 69 | 56.5 [390] | 0.036 |
| 73 | 55.9 [385] | 0.029 |
| 77 | 56.7 [391] | 0.091 |
| 80 | 56.6 [390] | 0.063 |
| 82 | 72.8 [502] | 0.091 |

The data shows the relationship between decreasing CO partial pressure and LIGAND B usage, with a large increase in ligand usage at a CO partial pressure of 38 psig (262 kPa) or lower. The high usage of LIGAND B returns to the previously seen lower values when the CO partial pressure is raised.

Comparative Experiment 2

LIGAND B Usage as a Function of Carbon Monoxide Partial Pressure and LIGAND B Concentration. (Not an Embodiment of the Invention)

The procedure of Comparative Experiment_1 is repeated, with the following exceptions. 3 liters of catalyst precursor comprising rhodium dicarbonyl acetoneate (75 ppm rhodium), LIGAND A (0.020 wt %; 0.33 mole equivalents per rhodium), LIGAND B (0.70 wt %; 15 mole equivalents per rhodium), tetraethylene glycol dimethyl ether (about 15% by weight) and mixed $C_4$ aldehyde (about 85 wt %, N:I of about 30:1) are charged to the reaction system. The product N:I is controlled at ~4 by maintaining a constant concentration of LIGAND A, whereas the concentration of LIGAND B is varied as a matter of study during the hydroformylation. The data for LIGAND B usage as a function of LIGAND B concentration at 35 and 65 psi (241 and 448 kPa) carbon monoxide is presented in Table 2 and Table 3 respectively.

TABLE 2

LIGAND B usage rates as a function of concentration, 35 psig (241 kPa) carbon monoxide

| Initial Ligand B:Rh molar ratio | Daily usage (g/L/day) |
|---|---|
| 3.996 | 0.102 |
| 4.723 | 0.189 |
| 5.380 | 0.160 |
| 6.146 | 0.186 |
| 6.973 | 0.156 |
| 7.292 | 0.151 |
| 12.667 | 0.174 |
| 13.955 | 0.149 |
| 14.516 | 0.189 |
| 14.706 | 0.209 |
| 15.860 | 0.225 |
| 15.937 | 0.251 |

TABLE 3

LIGAND B usage rates as a function of concentration, 65 psig (448 kPa) carbon monoxide

| Initial Ligand B:Rh molar ratio | Daily usage (g/L/day) |
|---|---|
| 4.907 | 0.017 |
| 5.668 | 0.030 |
| 5.745 | 0.033 |
| 5.881 | 0.042 |
| 6.201 | 0.021 |
| 7.406 | 0.041 |
| 8.547 | 0.038 |
| 8.581 | 0.048 |
| 8.620 | 0.040 |
| 11.900 | 0.060 |
| 15.305 | 0.084 |

The data show a positive correlation between LIGAND B concentration and usage rate. Additionally, the data show that the usage rate is significantly reduced by increasing the carbon monoxide partial pressure.

Comparative Experiment 3

Catalyst Stability During Start-Up without LIGAND A. (Not an Embodiment of the Invention)

The procedure of Example 1 is repeated, with the following exceptions. 2 liters of catalyst precursor comprising rhodium dicarbonyl acetylacetoneate (140 ppm rhodium), LIGAND B (10 mole equivalents per rhodium) tetraethylene glycol dimethyl ether (about 15% by weight) and mixed $C_5$ aldehydes (about 85% by weight, N:I of about 80:1) are charged to the reaction system. The reactors are heated to a reaction temperature of 85° C. under flowing carbon monoxide and hydrogen; the partial pressures of hydrogen and carbon monoxide are maintained at a 1:1 ratio over a range of 160-200 psig (1103-1379 kPa). Reactor 1 (Reactor 2 is bypassed) and 3 pressures are maintained at 230 and 210 psig (1586 and 1448 kPa) respectively. 1-butene is fed to Reactor 1 at a rate of 5 gram moles per liter of reactor volume per hour. A steady rhodium loss in the reactors of about 4.5 parts per million per day is observed from start-up. As the non-volatilize solution from the vaporizer is passed through the aqueous buffer treatment zone, the normally clear, colorless buffer is visibly darkened. Atomic Absorption (hereinafter AA) analysis on the aqueous buffer showed a rhodium concentration of 39 parts per million. The brownish colored buffer is analyzed by $^{31}P$ NMR, and shows no unexpected phosphorous resonances.

This demonstrates that when the reaction is initiated with rhodium and Ligand B alone, loss of valuable rhodium occurs.

Example 4

Catalyst Stability During Start-Up with LIGANDS A and B Present

In a manner analogous to Comparative Experiment 3, 2 liters of catalyst precursor comprising rhodium dicarbonyl acetylacetoneate (150 ppm rhodium), LIGAND B (20 mole equivalents per rhodium), LIGAND A (1.1 mole equivalents per rhodium), tetraethylene glycol dimethyl ether (about 15% by weight) and mixed $C_5$ aldehydes (about 85% by weight, N:I of about 80:1) are charged to the reaction system. The reactors are heated to a reaction temperature of 75° C. under flowing carbon monoxide and hydrogen; the partial pressures of hydrogen and carbon monoxide are maintained at a 1:1 ratio over a range of 160-200 psig (1103-1379 kPa). Reactor 1 (Reactor 2 is bypassed) and 3 pressures are maintained at 230 and 210 psig (1586 and 1448 kPa) respectively. 1-butene is fed to Reactor 1 at a rate of 5 gram moles per liter of reactor volume per hour. Rhodium concentration in the reactors is stable at 150 ppm over 48 hours of operation. As the non-volatilized solution from the vaporizer passes through the aqueous buffer treatment zone, the buffer remains clear in this example. AA analysis on the aqueous buffer after 48 hours shows a rhodium concentration of 2 parts per million. The clear buffer is analyzed by $^{31}P$ NMR, and shows no unexpected phosphorous resonances.

Ligand A concentration, as monitored by HPLC, slowly declines from an initial concentration of 1.1 moles relative to rhodium to 0.75 moles relative to rhodium over 5 days, while the ratio of normal to iso-aldehyde in the product (N:I) slowly declines from an initial value of about 80:1 to the desired value of about 6:1 over the same period. Rhodium accountability as measured by AA is nearly 100% throughout.

This demonstrates that when the hydroformylation catalyst is formed with at least one equivalent of the chelating bisphosphite, essentially no loss of rhodium occurs. Additionally, when the chelating bisphosphite is allowed to slowly degrade in the presence of an excess of the monophosphite, the desired final N:I may be reached and no loss of rhodium from the catalyst is observed.

Without wishing to be bound by any theory, it is believed that the excess chelating bisphosphite readily coordinates to the available catalytic metal, and thus mitigates loss of the valuable metal within the system.

Comparative Experiment 5

Catalyst Rate as a Function of LIGAND B Concentration. (Not an Embodiment of the Invention)

In a manner analogous to Example 1, 3 liters of catalyst precursor comprising rhodium dicarbonyl acetylacetoneate (70 ppm rhodium), LIGAND B (5 mole equivalents per rhodium) tetraethylene glycol dimethyl ether (about 25% by weight), LIGAND A (0.33 mole equivalents per rhodium) and mixed $C_4$ aldehydes (about 75% by weight, N:I of about 4:1) are charged to the reaction system. The reactors are heated to a reaction temperature of 70° C. under flowing carbon monoxide and hydrogen; the partial pressures of hydrogen and carbon monoxide are maintained at a 1:1 ratio over a range of 60-80 psig (414-552 kPa). Reactor 1, Reactor 2, and Reactor 3 total pressures are maintained at 130, 110 and 90 psig (896, 758, 621 kPa) respectively. Propylene is fed to Reactor 1 at a rate of 6.4 gram moles per hour. Ligand A is fed to the system at a rate of about 0.02 grams per liter of reactor volume per day to maintain N:I of the product at 4. The concentration of Ligand B is varied during the course of the hydroformylation. The results are summarized in Table 4.

TABLE 4

Aldehyde Product Rate as a Function of Ligand B:Rh molar ratio

| Days of Operation | Ligand B:Rh molar ratio | Total aldehyde rate, gmole/hr |
|---|---|---|
| 118 | 5.4 | 5.83 |
| 119 | 5.3 | 5.39 |
| 120 | 4.7 | 5.59 |
| 123 | 4.0 | 3.45 |
| 125 | 3.9 | 3.77 |
| 126 | 7.1 | 5.14 |
| 127 | 7.3 | 5.39 |
| 128 | 6.1 | 5.09 |

The data show that when the Ligand B:Rh molar ratio falls below 4.7 equivalents, a pronounced reduction in aldehyde formation rate is observed. It is also seen that the aldehyde rate is recovered upon increasing the Ligand B:Rh molar ratio to its previous value.

Example 6

Catalyst Rate as a Function of LIGAND B Concentration

The hydroformylation process is conducted in a glass pressure reactor operating in a continuous mode. The reactor consists of a three ounce pressure bottle partially submerged in an oil bath with a glass front for viewing. After purging the system with nitrogen, 20 ml of a freshly prepared rhodium catalyst precursor solution, the composition of which is shown below, is charged to the reactor with a syringe. After sealing the reactor, the system is purged with nitrogen and the oil bath is heated to furnish a reaction temperature of 80° C. The catalyst solution is activated with a feed of 1:1 CO and $H_2$ at a total operating pressure of 150 psig (1034 kPa) for 30 to 60 minutes. After the activation period, the reaction is initiated by the introduction of propylene. Flows of the individual gases are adjusted as desired, and nitrogen is added as necessary to maintain the desired total operating pressure of about 150 psig (1034 kPa). The flows of the feed gases ($H_2$, CO, propylene, $N_2$) are controlled individually with mass flow meters and the feed gases are dispersed in the catalyst precursor solution via fritted metal spargers. The partial pressures of $N_2$, $H_2$, CO, propylene, and aldehyde products are determined by analyzing the vent stream by gas chromatography (GC) and Dalton's Law. The unreacted portion of the feed gases is stripped out with butyraldehydes products by the nitrogen flow to maintain a substantially constant liquid level. The outlet gas is analyzed periodically by GC. Samples of the reaction fluid are withdrawn (via syringe) for $^{31}P$ NMR to determine the rate of decomposition of the ligands as a function of time under the reaction conditions. In practice, it is often observed that the system takes about one day to arrive at steady state conditions due to removing trace air from feed lines and reaching thermal equilibration of oil baths; so ligand studies are only initiated after steady state operations are achieved.

Catalyst precursor solutions containing rhodium dicarbonyl acetylacetonate (100 ppm Rh), Ligand B (5, 10 and 20 equivalents per rhodium) and tetraethylene glycol dimethyl ether (20 ml) as solvent are charged to each of three reactors. The reactors are pressurized with 50 psig (345 kPa) CO and 50 psig (345 kPa) hydrogen at 80° C. for about 1 hour prior to introduction of propylene. The moles of aldehyde produced per liter per hour divided by moles of olefin fed for each reactor (rate/olefin) is tabulated in Table 5:

TABLE 5

Reaction rate/olefin for Ligand B:Rh ratios of 5, 10 and 20:1.

| | Daily average for Rate/olefin | | |
|---|---|---|---|
| Days of operation | Ligand B:Rh = 5 | Ligand B:Rh = 10 | Ligand B:Rh = 20 |
| 1 | 1.37 | 1.62 | 2.43 |
| 2 | 0.73 | 1.03 | 1.87 |
| 3 | 0.49 | 0.69 | 1.42 |
| 4 | 0.45 | 0.69 | 1.18 |
| 5 | 0.44 | 0.38 | 1.12 |
| 6 | 0.41 | 0.45 | 1.06 |

The data show that the hydroformylation reaction rate is faster at higher Ligand B:Rh ratios, thus confirming that it is desirable to initiate a process with Ligand B at high concentrations.

Example 7

Rhodium Loss as a Function of LIGAND A Concentration

In a manner analogous to Example 6, catalyst precursor solutions containing rhodium dicarbonyl acetylacetonate (200 ppm Rh), Ligand B (20 equivalents per rhodium), the appropriate amount of Ligand A, and toluene (20 ml) are charged to each of five reactors. The reactors are pressurized with 75 psig (517 kPa) CO and 75 psig (517 kPa) hydrogen at a total flow of about 10 sL/hr at 80° C. After 5 minutes, 10 ml of degassed 0.04M sodium phosphate (pH 7.1) in water are added to each reactor via syringe. After 30 minutes of continuous flow the syngas is stopped and the layers are allowed to separate. The aqueous layers are sampled via syringe and the samples are analyzed using AA. The rhodium levels by AA appear in Table 6 and FIG. 1:

TABLE 6

Relationship between Ligand A concentration and rhodium loss.

| Rx | [Ligand A] (mole eq/Rh) | [Rh] ppm By AA* |
|---|---|---|
| 1 | 0 | 0.67 |
| 2 | 0.4 | 0.91 |
| 3 | 0.8 | 0.53 |
| 4 | 1.1 | 0.35 |
| 5 | 1.5 | 0.25 |

The data show that rhodium loss to the aqueous layer is reduced at higher Ligand A concentrations.

What is claimed is:
1. A process comprising (A) forming a hydroformylation catalyst by contacting under reaction conditions, in the presence of a solvent, a catalytic metal precursor, at least one organopolyphosphite ligand, CO, hydrogen, a bulky organomonophosphite ligand and, optionally, an olefin, wherein: the molar organopolyphosphite-to-catalytic metal ratio is greater than 1 but less than 2; the partial pressure of carbon monoxide is at least 25 psig; and the molar ratio of bulky organomonophosphite-to-catalytic metal is from 5:1 to 50:1; and then (B) allowing the organopolyphosphite ligand concentration to diminish such that the ratio of organopolyphosphite ligand-to-catalytic metal falls to less than 1, wherein the contacting is conducted such that the bulky organomonophosphite is introduced at the same time or after the organopolyphosphite ligand.

2. The process of claim 1 wherein the contacting is conducted such that the organopolyphosphite ligand and the catalytic metal precursor are introduced first, followed by addition of the bulky organomonophosphite.

3. The process of claim 1 wherein the organopolyphosphite and the catalytic metal precursor are contacted together prior to being contacted with the bulky organomonophosphite.

4. The process of claim 1 wherein the contacting is conducted such that the organopolyphosphite ligand is introduced first, followed by addition of the catalytic metal precursor, followed by addition of the bulky organomonophosphite.

5. The process of claim 1 wherein the partial pressure of carbon monoxide is from 30 psig to 250 psig.

6. The process of claim 1 wherein the at some point in step (A) molar organopolyphosphite-to-catalytic metal ratio is from 1.05 to 1.8.

7. The process of claim 1 wherein the at some point in step (A) molar organopolyphosphite-to-catalytic metal ratio is from 1.08 to 1.2.

8. The process of claim 1 wherein at some point in step (A) the amount of catalytic metal precursor is from 10 ppmw to 1,000 ppmw, calculated as free metal, based on the weight of the solvent, precursor, organopolyphosphite ligand, and organomonophosphite ligand.

9. The process of claim 1 wherein at some point in step (A) the amount of catalytic metal precursor is from 25 to 500 ppmw, calculated as free metal.

10. The process of claim 1 wherein at some point in step (A) the amount of catalytic metal precursor is from 50 to 350 ppmw, calculated as free metal.

11. The process of claim 1 wherein the catalytic metal of the catalytic metal precursor is rhodium.

12. The process of claim 1, further comprising providing the hydroformylation catalyst to a process for hydroformylating olefins to produce aldehydes.

13. The process of claim 12 wherein the partial pressure of carbon monoxide is from 30 psig to 250 psig.

14. The process of claim 12 wherein the molar ratio of bulky organomonophosphite-to-catalytic metal in step (B) is maintained at from 15:1 to 50:1.

* * * * *